(12) United States Patent
Chang

(10) Patent No.: US 7,611,488 B2
(45) Date of Patent: Nov. 3, 2009

(54) SAFETY HYPODERMIC SYRINGE

(76) Inventor: Komas Chang, No. 58-3, Sec. 1, Sanmin Rd., Taichung City (TW)

( * ) Notice: Subject to any disclaimer, the term of this patent is extended or adjusted under 35 U.S.C. 154(b) by 371 days.

(21) Appl. No.: 11/641,806

(22) Filed: Dec. 20, 2006

(65) Prior Publication Data

US 2008/0154193 A1 Jun. 26, 2008

(51) Int. Cl.
*A61M 5/00* (2006.01)
(52) U.S. Cl. ...................................... 604/110
(58) Field of Classification Search ............. 604/110, 604/192–198, 263, 221, 222, 225, 226, 229, 604/231, 218
See application file for complete search history.

(56) References Cited

U.S. PATENT DOCUMENTS 6,706,015 B2 * 3/2004 Bang ........................... 604/110

2004/0210198 A1 * 10/2004 Shih ............................ 604/218
2005/0240150 A1 * 10/2005 Gordon ....................... 604/110

* cited by examiner

*Primary Examiner*—Nicholas D Lucchesi
*Assistant Examiner*—Leah Stohr
(74) *Attorney, Agent, or Firm*—Rosenberg, Klein & Lee

(57) ABSTRACT

A safety hypodermic syringe formed of a barrel, a plunger, a locating block, a rubber stopper, a needle holder and a needle is disclosed. The plunger has a barbed front tip, which is forced into engagement with a hooked portion of the locating block when the plunger is pushed to the front end of the barrel so that the needle holder with the needle can be carried by the locating block to the inside of the barrel upon a backward movement of the plunger after the service of the syringe and biased with the locating block inside the barrel by means of the effect of a front pin of the rubber stopper.

2 Claims, 3 Drawing Sheets

SAFETY HYPODERMIC SYRINGE

BACKGROUND OF THE INVENTION

1. Field of the Invention

The present invention relates to a hypodermic syringe and more particularly, to a safety hypodermic syringe, which enables the needle holder and the needle to be received inside the barrel to avoid a re-use after the service of the safety hypodermic syringe.

2. Description of the Related Art

There are two ways to prevent accidental injury after the service of a hypodermic syringe. One way is to remove the needle from the barrel of the syringe by labor. The other way is to have the needle be received inside the barrel of the syringe. However, the received needle of a syringe after its service may still be forced out of the barrel to injure a person accidentally.

SUMMARY OF THE INVENTION

The present invention has been accomplished under the circumstances in view. It is the main object of the present invention to provide a safety hypodermic syringe, which keeps the needle holder and the needle received inside the barrel to avoid a re-use. According to one aspect of the present invention, the safety hypodermic syringe is comprised of a barrel, a plunger, a locating block, a rubber stopper, a needle holder, and a needle. The needle holder has a rear flange forced into engagement with an inner thread on the inside wall of an outer tube around an inner tube of the locating block so that the safety hypodermic syringe can suck in the prepared liquid medicine through the needle positively. According to another aspect of the present invention, the plunger has a barbed front tip, which is forced into engagement with a hooked portion of the locating block when the rubber stopper is moved with the plunger to the front end of the barrel to force liquid medicine out of the barrel, so that the needle holder with the needle can be carried by the locating block to the inside of the barrel upon a backward movement of the plunger after the service of the syringe. According to still another aspect of the present invention, the rubber stopper has a front pin, which causes the locating block to bias when the needle holder with the needle are carried by the locating block to the inside of the barrel, thereby keeping the needle received inside the barrel in a tilted manner. According to still another aspect of the present invention, the locating block has a toothed portion engaged with a toothed portion of the barrel to prevent rotation of the locating block relative to the barrel.

DETAILED DESCRIPTION OF THE PREFERRED EMBODIMENT

Figure 1:
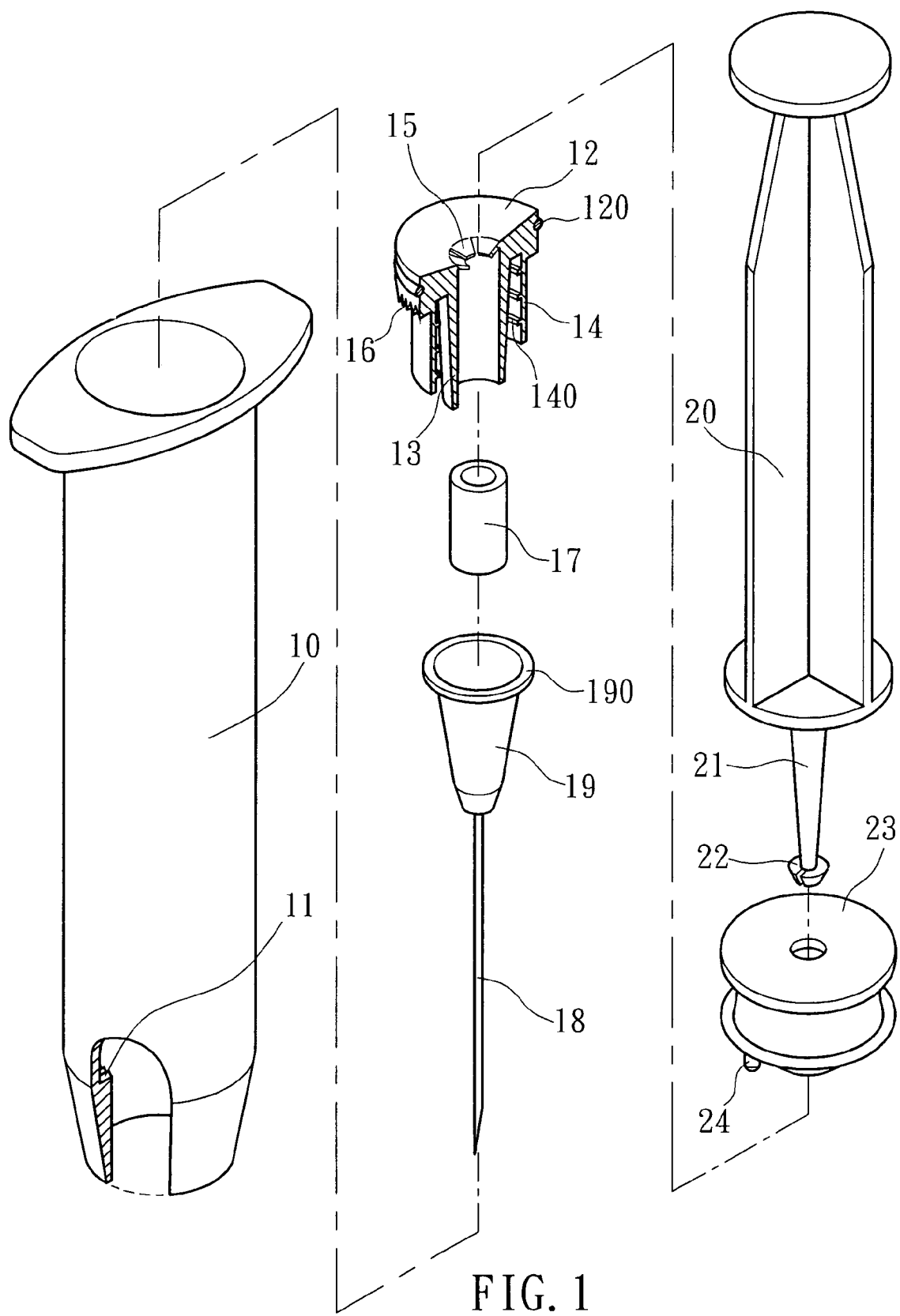
FIG. 1 is an exploded view of a safety hypodermic syringe in accordance with the present invention.
Figure 2:
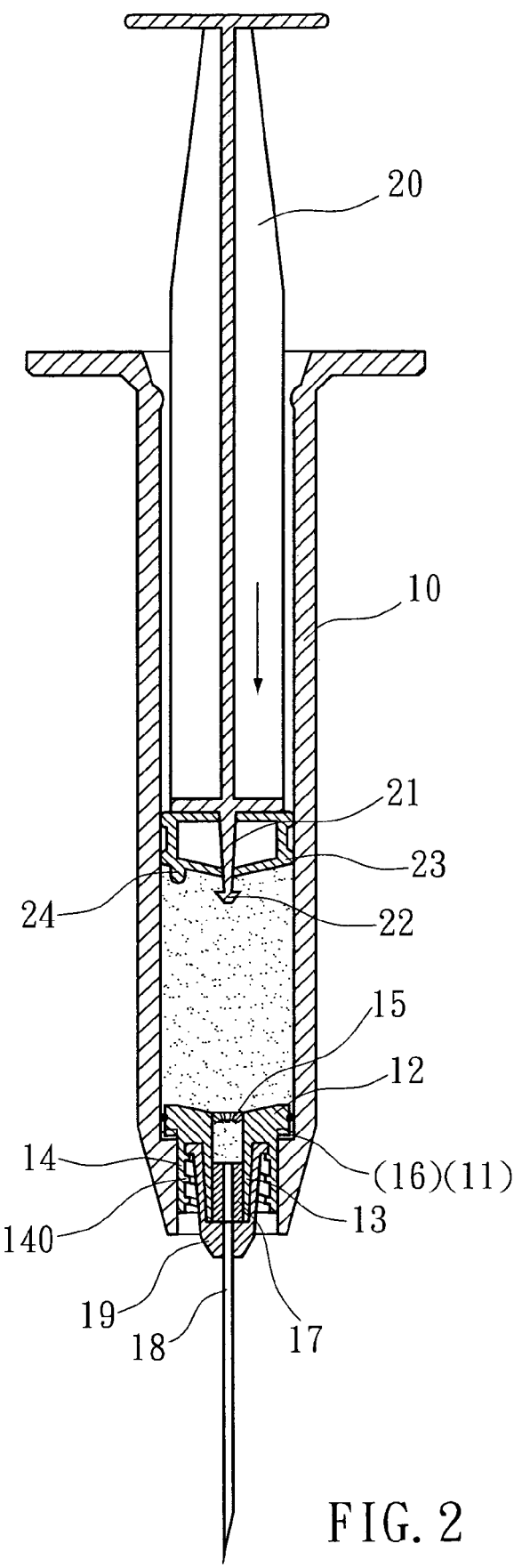
FIG. 2 is a sectional assembly view of the safety hypodermic syringe according to the present invention.

Referring to FIGS. 1~4, a safety hypodermic syringe in accordance with the present invention is shown comprised of a barrel 10, a locating block 12, needle holder 19, a needle 18, a plunger 20, and a rubber stopper 23.

The plunger 20 has a front extension rod 21, which holds the rubber stopper 23. The front extension rod 21 has a barbed front tip 22.

The rubber stopper 23 is fastened to the front extension rod 21 of the plunger 20, having a front pin 24 forwardly extending from the front side thereof near the border.

The locating block 12 is mounted with a gasket ring 120, having a forwardly extending outer tube 14, an inner thread 140 extending around the inside wall of the outer tube 14, an inner tube 13 coaxially suspending in the outer tube 14, a toothed portion 16 disposed outside the outer tube 14, and a hooked portion 15 in the rear end of the inner tube 13 for receiving the barbed front tip 22 of the plunger 20 so that the locating block 12 can be moved with the plunger 20 backwards to the inside of the barrel 10 to have the needle holder 19 and the needle 18 be received inside the barrel 10 after the service of the safety hypodermic syringe.

The needle holder 19 is inserted in between the outer tube 14 and inner tube 13 of the locating block 12 to hold the needle 18, having a rear flange 190 meshed with the inner thread 140.

The barrel 10 has a toothed portion 11 extending around the inside wall thereof near the front end for engaging the toothed portion 16 of the locating block 12 to prohibit rotation of the locating block 12 relative to the barrel 10.

Further, a filling tube 17 is fitted into the inner tube 13 of the locating block 12 to occupy a part of the inside space of the inner tube 13, thereby reducing accumulation of residual fluid medicine after the service of the safety hypodermic syringe.

Figure 3:
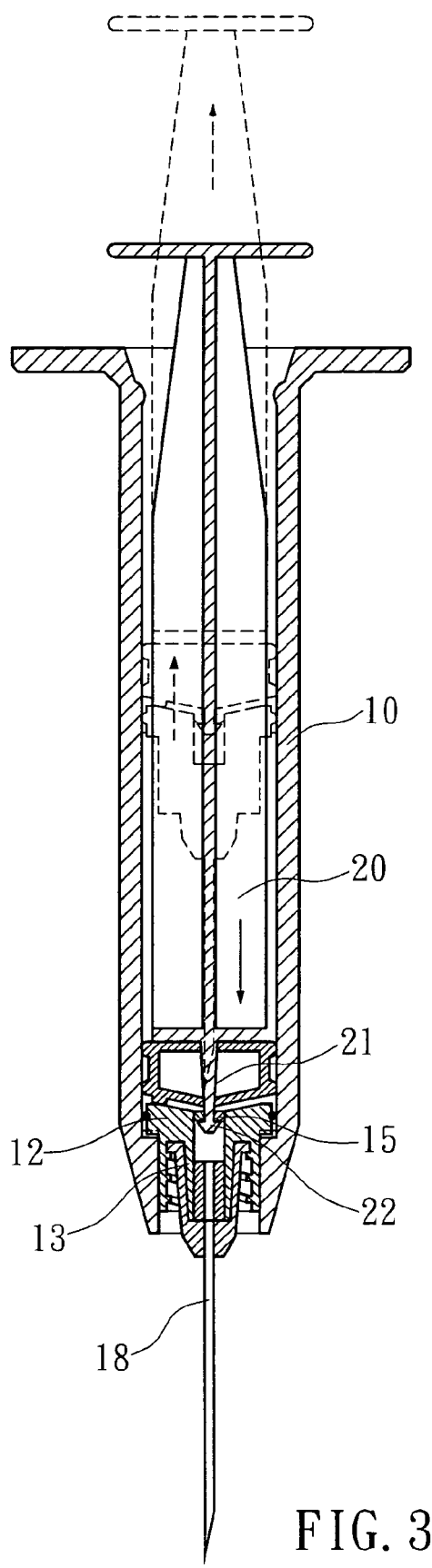
FIG. 3 is a schematic sectional view of the present invention, showing the needle holder and the needle pulled backwards with the plunger to the inside of the barrel.
Figure 4:
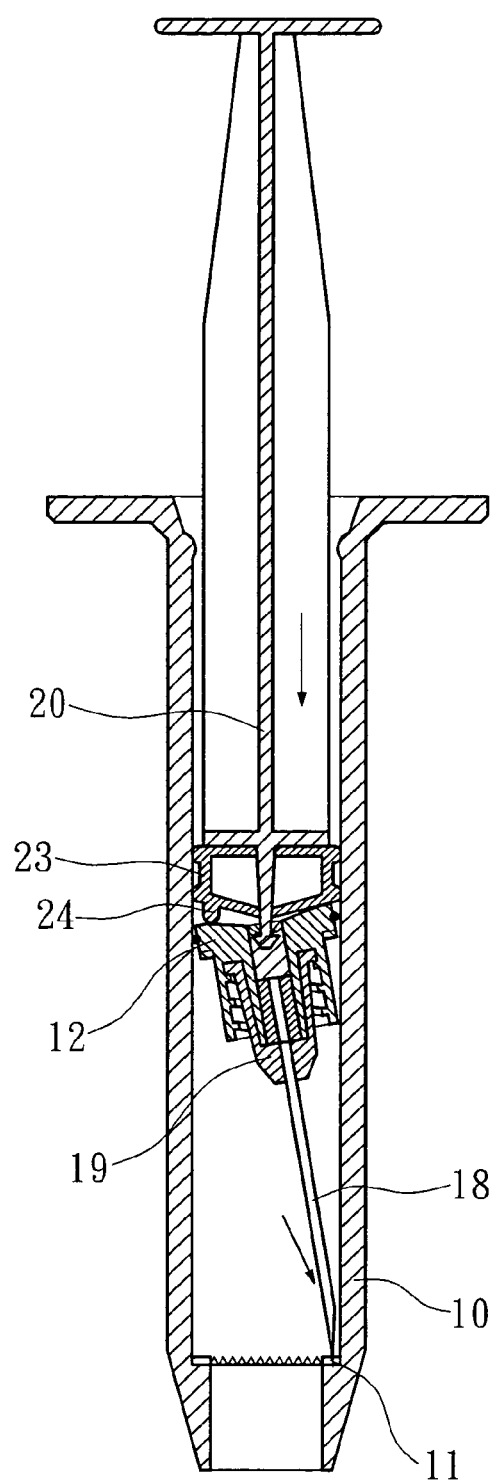
FIG. 4 corresponds to FIG. 3, showing the plunger pushed forwards to the front side of the barrel, the needle holder and the needle kept in the rear side inside the barrel.

The use of the safety hypodermic syringe is described hereinafter. At first, the rear flange 190 of the needle holder 19 is forced into engagement with the inner thread 140 so that the safety hypodermic syringe can suck in the prepared liquid medicine through the needle 18 (see FIG. 2). After the liquid medicine has been driven out of the barrel 10 into the patient's body, as shown in FIG. 3, the barbed front tip 22 of the plunger 20 is forced into engagement with the hooked portion 15 in the rear end of the inner tube 13. At this time, the user can pull the plunger 20 backwards to pull the locating block 12 and the needle holder 19 with the needle 18 to the inside of the barrel 10 (see FIG. 4). When the locating block 12 and the needle holder 19 with the needle 18 are moved to the inside of the barrel 10, the locating block 12 is forced by the front pin 24 to bias inside the barrel 10, thereby causing the needle 18 to be stopped against the toothed portion 11 of the barrel 10. When pushing the plunger 20 forwards again at this time, the needle 18 will be deformed inside the barrel 10 and will not be pushed out of the front side barrel 10.

As indicated above, the invention provides a safety hypodermic syringe that has the following features:

1. After the service of the safety hypodermis syringe, the barbed front tip 22 of the plunger 20 is forced into engagement with the hooked portion 15 in the rear end of the inner tube 13, allowing the needle 18 to be pulled backwards to the inside of the barrel 10 by the plunger 20.

2. The front pin 24 causes the locating block 12 to bias inside the barrel 10 when the locating block 12 is carried backwards by the plunger 20 to the inside of the barrel 10, and therefore the needle 18 is prohibited from being pushed out of the barrel 10 accidentally after the service of the safety hypodermic syringe.

3. Engagement between the toothed portion 11 of the barrel 10 and the toothed portion 16 of the locating block 12 prohibits rotation of the locating block 12 relative to the barrel 10.

4. The filling tube 17 is fitted into the inner tube 13 of the locating block 12 to occupy a part of the inside space of the inner tube 13, thereby reducing accumulation of residual fluid medicine after the service of the safety hypodermic syringe.

5. The rear flange 190 of the needle holder 19 is forced into engagement with the inner thread 140 so that the safety hypodermic syringe can suck in the prepared liquid medicine through the needle 18 positively.

A prototype of safety hypodermic syringe has been constructed with the features of FIGS. 1~4. The safety hypodermic syringe functions smoothly to provide all the features discussed earlier.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A safety hypodermic syringe comprising; a barrel, said barrel having a toothed portion extending around an inside wall near a front end thereof;

a locating block mounted with a gasket ring inside the front end of said barrel, said locating block having a forwardly extending outer tube, an inner thread extending around an inside wall of said outer tube, an inner tube coaxially suspending in said outer tube, a toothed portion disposed outside said outer tube and meshed with the toothed portion of said barrel to prohibit rotation of said locating block relative to said barrel, and a hooked portion in a rear end of said inner tube;

a needle holder inserted in between the outer tube and inner tube of said locating block to hold a needle, said needle holder having a rear flange meshed with said inner thread of said locating block;

a plunger axially movably inserted into said barrel, said plunger having a front extension rod, said front extension rod having a barbed front tip forced into engagement with the hooked portion of said locating block after said plunger has been pushed to the front end of said barrel for allowing said locating block and said needle holder with said needle to be pulled backwards to the inside of said barrel by said plunger; and a rubber stopper fastened to the front extension rod of said plunger, said rubber stopper having a front pin forwardly extending in eccentric manner from a perimeter thereof which allows asymmetric tilting contact of the locking block within the barrel.

2. The safety hypodermic syringe as claimed in claim 1, further comprising a filling tube fitted into said inner tube of said locating block.

* * * * *